(12) United States Patent
Sköldengen et al.

(10) Patent No.: US 6,553,260 B1
(45) Date of Patent: Apr. 22, 2003

(54) MEDICAL IMPLANT

(75) Inventors: Niklas Sköldengen, Täby (SE); Jan Lindberg, Sollentuna (SE); Hans Abrahamsson, Stockholm (SE); Kjell Helen, Bromma (SE); Tryggve Hemmingsson, Sollentuna (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/555,716
(22) PCT Filed: Nov. 27, 1998
(86) PCT No.: PCT/SE98/02155
§ 371 (c)(1),
(2), (4) Date: Jun. 1, 2000
(87) PCT Pub. No.: WO99/27992
PCT Pub. Date: Jun. 10, 1999

(30) Foreign Application Priority Data

Dec. 4, 1997 (SE) .............................. 9704521

(51) Int. Cl.[7] ................................ A61N 1/18
(52) U.S. Cl. .................. 607/27; 607/29; 607/32
(58) Field of Search .................. 607/27, 29, 32, 607/60; 128/903

(56) References Cited

U.S. PATENT DOCUMENTS

| 4,390,020 A | 6/1983 | Herpers |
|---|---|---|
| 4,416,282 A | 11/1983 | Saulson et al. |
| 4,445,512 A | 5/1984 | Krupka et al. |
| 4,488,555 A | 12/1984 | Imran |
| 4,614,192 A | 9/1986 | Imran et al. |
| 5,321,618 A | 6/1994 | Gessman |
| 5,433,736 A | 7/1995 | Nilsson |
| 5,591,213 A | 1/1997 | Morgan |
| 5,891,178 A * | 4/1999 | Mann et al. |
| 5,891,180 A * | 4/1999 | Greeninger et al. .......... 607/32 |
| 6,247,474 B1 * | 6/2001 | Greeninger et al. ........ 128/899 |
| 6,370,433 B1 * | 4/2002 | Hartlaub et al. ............. 607/32 |

OTHER PUBLICATIONS

Chapter Entitled "Electrotherapy of the Heart" from "Technical Achievement of the Dual–Chamber Pacemaker," Schaldach (1992), pp. 61–65.

* cited by examiner

Primary Examiner—Mark Bockelman
(74) Attorney, Agent, or Firm—Schiff Hardin & Waite

(57) ABSTRACT

A medical implant such as a heart stimulator has a detector which detects an extracorporeally generated interrogation signal for at least one predetermined working parameter of the medical implant. The interrogation signal is generated by an interrogation signal device capable of only unidirectional communication to the medical implant. The implant includes a response signal generator which generates an extracorporeal detectable response signal, detectable, for example, by a stethoscope, which indicates only if the interrogated working parameter has a satisfactory value or a non-satisfactory value.

7 Claims, 1 Drawing Sheet

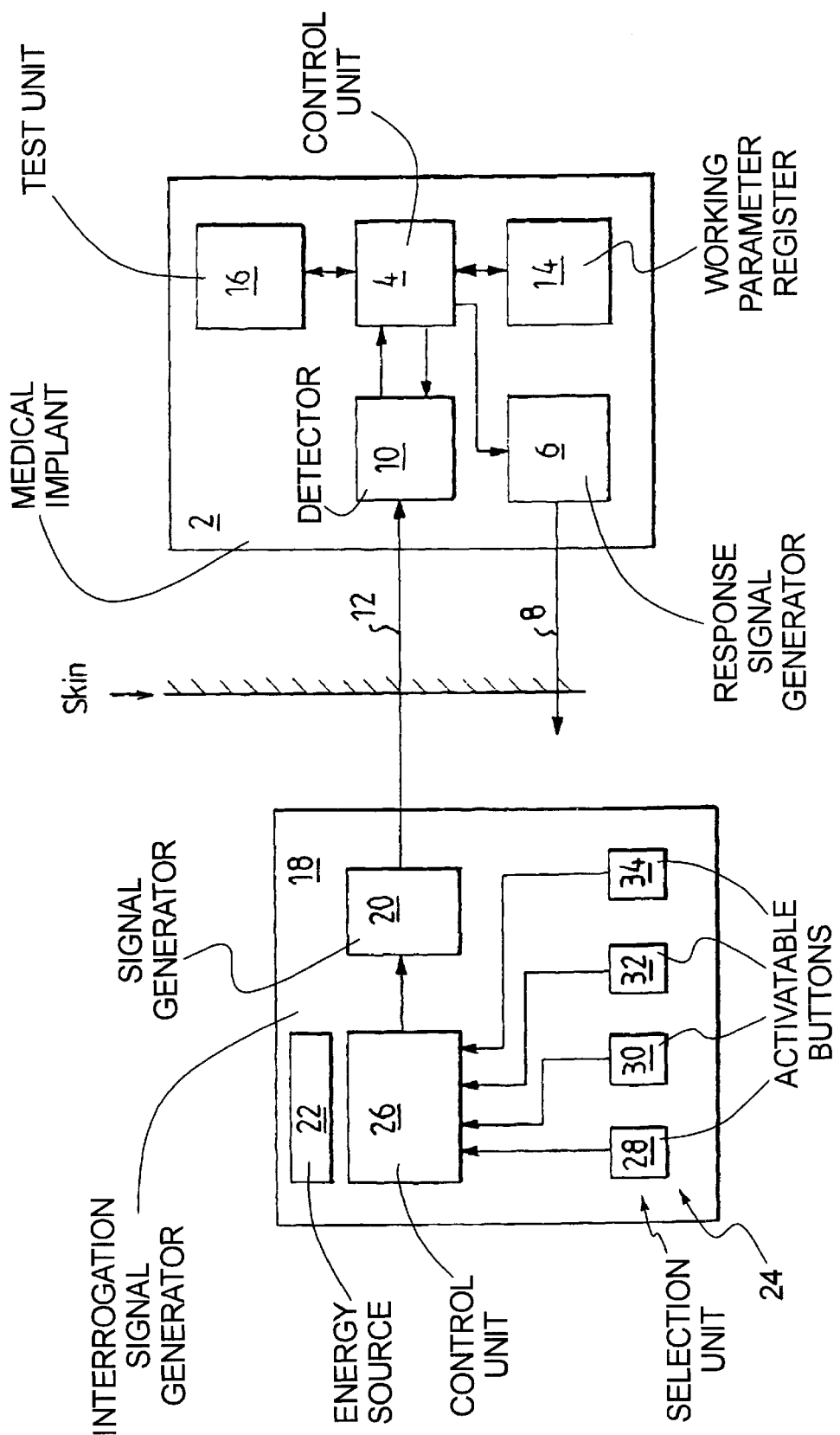

MEDICAL IMPLANT

BACKGROUND OF THE INVENTION

1. Field of the Invention

The present invention is directed to a medical implant of the type which generates an extracorporeally detectable signal in response to an interrogation signal, as well as to an interrogation signal generator for generating such an interrogation signal.

2. Description of the Prior Art

In a normal follow-up for a pacemaker patient many different working parameters of the pacemaker are tested, e.g. battery status, stimulation threshold, electrode lead impedance and others. The follow-up is made in a hospital at least once per year and the physician uses a bi-directional communication programmer that communicates with the pacemaker by radio waves. The requested information is received by the programmer and analyzed by the physician, which is a difficult and time-consuming job. The programmer is quite expensive and may not always be a part of the ordinary equipment for every small-sized hospital. Battery tests can also be performed by putting a magnet over the pacemaker that changes the stimulation rate in dependence of the battery status. This rate can be seen on an ECG machine or by listening for or feeling the pulse. Devices used for performing battery tests are for instance disclosed in U.S. Pat. No. 54,390,020 and U.S. Pat. No. 4,416,282.

In U.S. Pat. No. 4,390,020 a programmable pacemaker is disclosed capable of operating in several stimulating modes, having battery powered stimulating means and stimulating mode selector means. Sensing and evaluating means, which can be activated externally by means of a magnet, for example at a medical examination, monitor the terminal voltage of the battery and cause the pacemaker via the stimulating selector means to change operation from a first stimulating mode with a programmed stimulation rate to a mode with a fixed stimulation rate, when the terminal voltage decreases below a first threshold value and operate in a second predetermined stimulating mode at a fixed stimulation rate when the terminal voltage decreases below the first as well as a lower second threshold value.

U.S. Pat. No. 4,416,282 discloses a similar pacemaker which also includes sensing and evaluating means for monitoring of the battery capacity with regard to two battery depletion levels. The stimulation rate automatically decreases with the decreasing of the battery capacity below the depletion levels.

In U.S. Pat. No. 4,488,555 a battery condition warning system for a medical implant is known. The warning system generates an audible alarm to warn the patient of an impending battery failure.

In U.S. Pat. No. 4,614,192 an implantable cardiac defibrillator is disclosed, providing, upon magnet-type interrogation, an audible indication to verify the status of the implanted device. To enable the defibrillator to deliver a defibrillating pulse a control circuit must be placed in an active state. To place it in an active state a ring magnet is used to toggle a status flip-flop that emits an enabling signal to the control circuit. At the same time, an audio oscillator is energized by the output signal from the status flip-flop and from a rate circuit, enabling the audio oscillator to emit sounds synchronous with the heart beat if a bipolar electrode is properly positioned within the heart and to emit a continuous tone if the defibrillator is inactive and properly positioned. Absence or presence of an audible tone indicates whether the probe is properly lodged about the right ventricle. The audible indication in the defibrillator disclosed in U.S. Pat. No. 4,614,192 is generated in response of a magnet interrogation and reflects the status of the implant at the time the interrogation is made, i.e. the measurement procedure is performed at that time.

One drawback for many of these known solutions is that some kind of more or less complicated technical equipment is needed, e.g. a programmer or an ECG-machine, not always available in smaller clinics.

Another drawback is that before the implant can respond to an interrogation from an external device, often time-consuming tests has to be performed by the implant.

SUMMARY OF THE INVENTION

An object of the Invention is to provide a medical implant capable of immediately generating an response signal that is easy to recognize outside the body by e.g. a stethoscope, and that reflects the present status of at least one predetermined working parameter of the implant. Another object is for the response signal indicates if the working parameter has a satisfactory value or not.

One further object of the invention is to provide an interrogation signal-generating device adapted to work with a medical implant which achieves the above objects.

The above objects are achieved in a medical implant in accordance with the principles of the present invention which contains a predetermined number of working parameter status registers, each containing updated data representing a first state or a second state of a working parameter, the first state indicating that the working parameter has a satisfactory value and the second state indicating that the working parameter has a non-satisfactory value and wherein, in response to detection of an interrogation signal inquiring about a status of a particular working parameter, the medical implant generates a response signal which only identifies the content of the status register for the working parameter which was the subject of the interrogation signal, and the response signal is extracorporeally detectable.

Since the response signal indicates only whether the inquired-about working parameter has a satisfactory value or a non-satisfactory value, it can be very simply extracorporeally detected, such as by a stethoscope or tactilely, depending on the type of response signal which is generated. Since the response signal has only one of two possible states, there is no need to analyze the signal beyond identifying its state.

The above objects are also achieved in an interrogation signal generator, which operates with a medical implant as described above, which is adapted only for one-way signaling to the medical implant. The interrogation signal generator contains only a signal generator, an energy source, a control unit and a selection unit which is used to activate the signal generator to generate an appropriate interrogation signal regarding a particular working parameter.

DESCRIPTION OF THE DRAWING

The single FIGURE is a schematic block diagram of a medical implant and an interrogation signal generator constructed and operating in accordance with the principles of the present invention.

DESCRIPTION OF THE PREFERRED EMBODIMENTS

In the figure the medical implant 2 and the interrogation signal generating device 18 are shown in a block diagram.

The medical implant 2, e.g. a pacemaker or a defibrillator, contains a first control unit 4 connected to a response signal generator 6, an interrogation signal detector parameter status registers 14 and a test unit 16. As is well-known to those skilled in the art the medical implant 2 also includes inter alia an energy source, one or many electrode leads for applying stimulation pulses to the tissue etc. For simplicity, however, these features are not described in detail neither in the FIGURE nor in the description since they are not a part of the invention and their functions are well known to persons skilled in the art.

The interrogation signal generating device 18 includes only a signal generator 20 adapted to generate an interrogation signal 12, an energy source 22, selection unit 24 with a predetermined number of activation buttons 28, 30, 32, 34 (four in the FIGURE) and a control unit 26. Each activation button 28, 30, 32, 34 represents at least one working parameter of the medical implant 2. The working parameters could be e.g. the battery status, the status of lead impedance or the status of a stimulation threshold. One of the activation buttons 28, 30, 32, 34 represents the overall status of all working parameters together.

The medical implant 2 and the interrogation signal generating device 18 work together in the following way: The person who is going to interrogate the implant 2 places the device 18 on the skin of a patient above the implant 2, and presses one of the activation buttons 28, 30, 32, 34 causing the control unit 26 to activate the signal generator 20 to generate an interrogation signal 12. The working parameter represented by the pressed activation button is univocally identified by the generated interrogation signal 12.

The interrogation signal is preferably a radio-wave signal having a frequency in the range 2–8 kHz. A predetermined communication protocol is used enabling said univocal identification of the interrogation signal 12. According to an alternative embodiment the interrogation signal is a magnetic signal 12. Interrogation is then made by placing a device capable of generating magnetic field of a predetermined kind, e.g. a magnet, on the skin close to the implant.

The interrogation signal 12 is detected by the interregation signal detector 10 in the medical implant 2. According to a preferred embodiment the telemetry coil, normally used for ordinary communication between an external programming device and a medical implant, is used for detecting the interrogation signal 12. Since this technique is well known to those skilled in the art it need not be described herein. The detected interrogation signal 12 is applied to the control unit 4 which addresses the working parameter status register 14 that matches the requested working parameter. The content of the addressed status register is read by the control unit 4 which then activates the response signal generator 6 to generate a response signal 8 which is detectable outside the body of the implant wearer.

According to a first preferred embodiment the response signal 8 is an acoustic signal generated by an acoustic signal generator, e.g. a piezoelectric crystal. The frequency of the generated acoustic tone could be in the range of 100–1900 Hz, preferably 1000–1900 Hz where 1400 Hz is a preferred value. The tone should be strong enough to be able to be detected by a stethoscope placed on the skin close to the implant. When an interrogation signal 12 is detected by the interrogation signal detector 10 the control unit 4 identifies the working parameter status register requested by the interrogation signal 12. The value, "satisfactory" or "non-satisfactory", in the requested register is read out by the control unit 4 and the response signal generator 6 is activated to generate the response signal 8, in this embodiment an acoustic signal. The response signal generator is preferably active during 5 minutes and generates a response signal every $15^{th}$ second. The response signal 8 representing the states "satisfactory" or "non-satisfactory" can of course be chosen in many different ways, e.g. "satisfactory" could be represented by five short tones followed by five long tones, and "non-satisfactory" could be represented by the sequence three short tones, three long tones and three short tones.

According to a second preferred embodiment the response signal 8 is represented by a predetermined change of the stimulation frequency. This change in frequency can be palpated directly, detected by a stethoscope or studied on a print-out from an ECG-equipment.

When, according to this second preferred embodiments, an interrogation signal 12 is detected by the interrogation signal detector 10, the control unit 4 changes, if necessary, the pacing mode to V00, that is ventricular stimulation with no sensing and no inhibition possible, and the stimulation rate to a predefined rate related to the state of the interrogated working parameter. The state "satisfactory" could e.g. be represented by a stimulation rate per minute of 100 and the state "non-satisfactory" could then be represented by a rate of 80.

If the interrogation signal 12 is a radio-wave signal this predefined rate preferably could last for e.g. 32 pacing intervals and if the interrogation signal 12 is a magnetic signal, as long as the magnetic field is present.

By continuously updating the working parameter status registers 4 the response signal can be generated almost immediately because no time-consuming tests of the different working parameters has to be performed. The working parameters of the medical implant 2 could be, as indicated above, e.g. the battery status, the status of lead impedance or the status of the stimulation threshold. One of the activation buttons 28, 30, 32, 34 represents the overall status of all working parameters together.

The most commonly used battery in modern pacemakers is the lithium-iodine battery. As current is drained from the battery an increase in the internal impedance of the battery occurs. Since the rate of increase in battery impedance versus time at any specific battery current drain is known, measured battery current drain and battery impedance allow prediction of remaining device longevity. In practice, the internal impedance is measured at regular intervals, e.g. every $24^{th}$ hour, and compared to a predetermined threshold representing an impedance value corresponding to the recommended replacement time (RRT), being e.g. 2 years. The battery status is given the state "satisfactory" if the RRT is more than e.g. 2 years and the state "non-satisfactory" if less than 2 years.

A very vital part of a pacemaker system is the electrode lead connecting the pacemaker to the inside of the heart. The electrode -lead is inserted into the heart via e.g. a great vein and comprises an electrical lead insulated by e.g. silicone. The function of an electrode lead can be tested, by measuring of the lead impedance. If the lead impedance is decreased, it can be caused by a breakdown or damage in the insulation of the lead, and if the lead impedance is increased it can be caused by a break or damage of the electrical lead. The lead impedance can be measured e.g. by an lead impedance scanning system disclosed in U.S. Pat. No. 4,899,750. In this system the voltage difference over a sample capacitor, before and after the delivery of a pacing pulse, is used in an equation to calculate the lead impedance. If the lead impedance is in the range of e.g. 750+/−500 Ohm the status of lead impedance is given the state "satisfactory" and if outside said range the state "non-satisfactory".

For the stimulation threshold, for the ventricle and/or the atrium, the state is given the value "satisfactory" if the threshold is below a predetermined value, e.g. 3 Volts and "non-satisfactory" if the threshold is above said value. It is of course only possible to test the stimulation threshold if some kind of automatic search for the stimulation threshold can be performed, e.g. according to the AUTOCAPTURE™-algorithm, at regular intervals.

All the values used to determine if the state is "satisfactory" or "non-satisfactory" for the working parameters can of course be individually set in dependence of the circumstances.

As indicated above one of the working parameter status registers reflects the combined status of all working parameters in the way that if any of the other working parameters is in the "non-satisfactory"-state the combined status will be "non-satisfactory". When the interrogation signal 12 is a magnetic signal, in accordance with the above-mentioned alternative embodiment, the response signal 8 reflects the content of the register with the combined status.

As indicated above the values stored in the working parameter status registers are updated continuously as a result of tests performed by said the test unit 16.

It is apparent to those of skill in the art that working parameters other than the above described can be used, e.g. if a certain level for a predetermined parameter is exceeded more than a predetermined number of times the state is set to "non-satisfactory". In general, if a predetermined event occurs (related to the heart or the pacemaker), that not fulfills the "satisfactory" criteria, the state for that working parameter is set to "non-satisfactory".

Although modifications and changes may be suggested by those skilled in the art, it is the intention of the inventors to embody within the patent warranted hereon all changes and modifications as reasonably and properly come within the scope of their contribution to the art.

What is claimed is:

1. A medical implant comprising:

means for administering a medical therapy having a plurality of working parameters associated therewith;

a plurality of working parameter status registers, each of status registers containing a continually updated status indicator for one of said working parameters, said status indicator having either a first state indicating that the working parameter associated with the status registers has a satisfactory value, or a second state indicating that the working parameter associated with the status register has a non-satisfactory value, said status indicator having no other state;

a detector adapted to receive an extracorporeally generated interrogation signal regarding one of said working parameters, and emitting a detector output signal identifying said one of said working parameters;

a control unit supplied with said detector output signal and connected to each of said working parameter status registers, said control unit addressing the status register for said one of said working parameters and reading out the status indicator thereof; and a response signal generator connected to said control unit and supplied with said status indicator, said response signal generator emitting an extracorporeally detectable response signal dependent on the status indicator supplied by said control unit, said response signal having a first response signal state corresponding to said first state of said status indicator and a second response signal state corresponding to said second state of said status indicator, and no other response signal state.

2. A medical implant as claimed in claim 1 comprising a test unit for monitoring said plurality of working parameters and being connected to said plurality of status registers and automatically updating the respective status registers at predetermined intervals.

3. A medical implant as claimed in claim 1 wherein said plurality of working parameters include a working parameter identifying an overall status of all of said plurality of working parameters.

4. A medical implant as claimed in claim 1 wherein said response signal generator generates an acoustic signal as said response signal.

5. A medical implant as claimed in claim 1 wherein said response signal generator comprises an stimulation pulse generator which generates stimulation pulses as a part of said medical therapy and wherein said response signal generator further comprises electrode leads adapted for delivering said stimulation pulses to a heart, said stimulation pulses having a frequency, and wherein said response signal comprises a signal having a predetermined change of said stimulation frequency.

6. A medical implant as claimed in claim 1 wherein said response signal generator generates a stethoscope-identifiable signal as said response signal.

7. A medical implant as claimed in claim 1 wherein said response signal generator generates a magnetic signal as said response signal.

* * * * *